United States Patent [19]

Wiesehahn et al.

[11] Patent Number: 5,176,921

[45] Date of Patent: Jan. 5, 1993

[54] METHOD OF BLOOD COMPONENT DECONTAMINATION BY GLUCOSE ADDITION

[75] Inventors: Gary P. Wiesehahn, Alameda; Laurence Corash, San Francisco, both of Calif.

[73] Assignees: Diamond Scientific Co., Des Moines, Iowa; University of California, Oakland, Calif.

[21] Appl. No.: 350,335

[22] Filed: May 11, 1989

Related U.S. Application Data

[63] Continuation-in-part of Ser. No. 164,915, Mar. 7, 1988, which is a continuation of Ser. No. 928,841, Oct. 20, 1986, Pat. No. 4,748,120, which is a continuation of Ser. No. 490,681, May 2, 1983, abandoned.

[51] Int. Cl.$^5$ ............................................. A61K 35/14
[52] U.S. Cl. .................................... 424/529; 424/532; 424/530; 424/85.8; 435/2; 514/2; 514/8
[58] Field of Search .................... 435/2; 424/529, 533, 424/532, 530, 85.8; 514/2, 8

[56] References Cited

U.S. PATENT DOCUMENTS

| | | | |
|---|---|---|---|
| 3,874,384 | 4/1975 | Deindoerfer et al. | 435/2 |
| 4,112,070 | 9/1978 | Harmening | 424/533 |
| 4,124,598 | 11/1978 | Hearst et al. | |
| 4,160,204 | 9/1979 | Hearst et al. | |
| 4,321,919 | 3/1982 | Edelson | |
| 4,327,086 | 4/1982 | Fukushima et al. | |
| 4,568,542 | 2/1986 | Kronenberg | |
| 4,572,899 | 2/1986 | Walker et al. | 424/533 |
| 4,595,653 | 6/1986 | Kronenberg | |
| 4,695,460 | 9/1987 | Holme | 424/532 |
| 4,748,120 | 5/1988 | Wiesehahn | 435/173 |

OTHER PUBLICATIONS

Musajo, et al., *Experentia*, vol. XXI, pp. 22–24 (1965).
De Mol, et al., *Photochemistry and Photobiology*, vol. 33, pp. 815–819 (1981).
Veronese, et al., *Photochemistry and Photobiology*, vol. 36, pp. 25–30 (1982).
De Mol, et al., *Chemical Interactions*, vol. 95, No. 74467, p. 197 (1981).
De Mol, et al., *Photochemistry ad Photobiology*, vol. 34, pp. 661–666 (1981).
Veronese, et al., *Photochemistry and Photobiology*, vol. 34, pp. 351–354 (1981).
Singh, et al., *Photochemistry and Photobiology*, vol. 28, pp. 539–545 (1978).
Joshi, et al., *Biochemical and Biophysical Research Communications*, vol. 112, No. 2, pp. 638–646 (1983).
Grossweiner, *NCI Monograph*, No. 66, pp. 47–54.
Hanson, *Medical Virology II*, pp. 45–79.
Rodighiero and Dall'Acqua, *NCI Monograph*, No. 66, pp. 31–42 (1982).
Hyde, et al., *Biochemistry*, vol. 17, pp. 1251–1257 (1978).
Hanson, et al., *J. Gen. Virology*, vol. 40, pp. 345–358 (1978).
Swanstrom, et al., *J. Gen. Virology*, vol. 113, pp. 613–622 (1981).
Redfield, et al., *Infec. and Immun.*, vol. 32, pp. 1216–1226 (1981).
Cremer, et al., *J. Clin. Microbiology*, vol. 15, pp. 815–823 (1982).

*Primary Examiner*—Sam Rosen
*Attorney, Agent, or Firm*—Joseph C. Gil; Lyndanne M. Whalen

[57] ABSTRACT

Biological compositions are freed of functional polynucletides by treatment of the biological composition with psoralen derivatives under irradiation conditions in which the proteins retain their original physiological activities and any polynucleotide present is rendered inactive. More specifically blood components are decontaminated of viruses by the addition of psoralen and irradiation and thereafter adding glucose.

5 Claims, No Drawings

METHOD OF BLOOD COMPONENT DECONTAMINATION BY GLUCOSE ADDITION

CROSS REFERENCE TO RELATED APPLICATIONS

This application is a continuation-in-part of Ser. No. 164,915 filed Mar. 7, 1988, which is itself a continuation of Ser. No. 928,841 filed Oct. 20, 1986, and now U.S. Pat. No. 4,748,120, which is itself a continuation of Ser. No. 490,681 filed May 2, 1983 and now abandoned.

BACKGROUND OF THE INVENTION

1. Field of the Invention

Recipients of blood and blood components risk acquiring infections from foreign biological organisms, either pre-existing in the blood at the time of collection or transmitted to the blood product during manipulation. Medical personnel who are in contact with collected human blood or clinical samples also have a significant chance of being exposed to potentially lethal blood-borne or sample-borne biological organisms. Blood components today are obtained from blood donors and frequently involve pooled lots, where one or more of the donors may be harboring a viral, bacterial or other infection. Since the blood or blood components are required to provide physiological functions in a mammalian host, normally a human host, these functions must not be impaired by the decontamination treatment of the biological composition. In addition, the blood or blood components may not be modified in such a way as to make them immunogenic which could result in an adverse immune response Finally, any treatment should not leave residues or products detrimental to the health of the host or such residues or products should be readily removable.

2. Description of the Prior Art

U.S. Pat. No. 4,327,086 describes the method for heat treating an aqueous solution containing human blood coagulation factor XIII. U.S. Pat. No. 4,321,919 proposes extracorporeal treatment of human blood with 8-methoxypsoralen (8-MOP). Hyde and Hearst, Biochemistry (1978) 17:1251-1257, describe the binding of two psoralen derivatives to DNA and chromatin. Musajo et al., Experientia (1965) XXI, 22-24, describe photo-inactivation of DNA-containing viruses with photosensitizing furocoumarins. U.S. Pat. Nos. 4,350,594, 4,348,283 and 4,350,156 describe filtration methods for selective removal of blood components based on molecular weight. U.S. Pat. No. 4,329,986 describes extracorporeal treatment of blood with a chemotherapeutic agent which is subsequently removed by dialysis. The July/August 1982 issue of Genetic Engineering News proposed the use of psoralens to sterilize "clinical or commercial reagents or instruments."

Some data showing substantial impairment of the biological function of certain enzyme proteins using furocoumarins are published in the scientific literature (see for example, Veronese, F.M. et al., Photochem. Photobiol. 34:351 (1981); Veronese, F.M. et al., Photochem. Photobiol. 36:25 (1982).

SUMMARY OF THE INVENTION

Compositions for use in mammalian hosts may be decontaminated by treatment by furocoumarins and long wavelength ultraviolet (UVA) light. In this improved process, immediately following the decontamination, particularly of blood platelets, glucose is added and a post-decontamination gassing may also be employed in order to minimize risk of damage to blood platelets.

DESCRIPTION OF THE SPECIFIC EMBODIMENTS

In accordance with the subject invention, compositions to be employed with mammalian hosts, which may harbor polynucleotides capable of detrimental physiological effects in a host, are combined with furocoumarin compositions and treated with UVA light under predetermined conditions, whereby the physiological activities of the non-nucleic acid components are retained. (Whenever the term "polynucleotide" is used in this application it should be understood to mean: (1) microorganisms containing nucleic acids (either DNA or RNA), (2) nucleic acid genomes or sub-genomic fragments from microorganisms, from procaryotes or from eucaryotes, or (3) any other nucleic acid fragments.)

In decontaminating the biological composition, an aqueous medium containing the biological preparation is combined with an appropriate amount of the furocoumarin composition and irradiated with ultraviolet light under conditions where all of the polynucleotide is inactivated, while the components other than nucleic acid retain their normal physiological activities.

Various biological compositions may be employed, particularly protein compositions involving blood or blood components. Whole blood, packed red cells, platelets, and plasma (fresh or fresh frozen plasma) are of interest. Other blood components of interest include plasma protein portion, antihemophilic factor (AHF, Factor VIII); Factor IX and Factor IX complex (Factors II, VII, IX and X); fibrinogens, Factor XIII, prothrombin and thrombin (Factor II and IIa); immunoglobulins (e.g., IgA, IgD, IgE, IgG and IgM and fragments thereof e.g. Fab, F(ab')$_2$, Fc); hyper-immune globulins as used against tetanus and hepatitis B; cryoprecipitate; albumin; interferons; lymphokines; transfer factors; etc. Other biological compositions include vaccines, recombinant DNA produced proteins, oligopeptide ligands, etc. The protein concentration in the aqueous medium will generally range from about 1 ug/ml to 1 gm/ml, more usually from about 1 mg/ml to 100 mg/ml. The pH will normally be close to physiologic pH (7.4), generally in the range of about 6 to 9, more usually about 7. Other components may be present in the medium, such as salts, additives, buffers, stabilizers, or the like. These components will be conventional components, which will be added for specific functions.

The furocoumarins will include psoralen and derivatives, where the substituents will be: alkyl, particularly of from 1 to 3 carbon atoms, e.g. methyl; alkoxy, particularly of from 1 to 3 carbon atoms, e.g. methoxy; and substituted alkyl, of 1 to 6, more usually 1 to 3 carbon atoms having from 1 to 2 heteroatoms, which will be oxy, particularly hydroxy or alkoxy of from 1 to 3 carbon atoms, e.g. hydroxymethyl and methoxymethyl, or amino, including mono- and dialkyl amino having a total of from 1 to 6 carbon atoms, e.g. aminomethyl. There will be from 1 to 5, usually 2 to 4 substituents, which will normally be at the 4, 5, 8, 4' and 5' positions, particularly at the 4'-position. Illustrative compounds include 5-methoxypsoralen, 8-methoxypsoralen (8-MOP), 4, 5',8-trimethylpsoralen (TMP), 4'-hydroxymethyl-4,5'8-trimethylpsoralen (HMT), 4'- aminomethyl-4,5',8-trimethylpsoralen (AMT), 4-methylpsoralen, 4,4'-dimethylpsoralen, 4,5'-dimethylpsoralen, 4',8-dimethylpsoralen, and 4'-methoxymethyl-4,5',8-trimethylpsoralen.

The subject furocoumarins are active with a wide variety of viruses and other polynucleotides, DNA or RNA, whether single stranded or double stranded. Illustrative viruses include: adenovirus, arenavirus, bacteriophage, bunyavirus, herpesvirus, orthomyxovirus, papovavirus, paramyxovirus, picornavirus, poxvirus, reovirus, retrovirus, rhabdovirus, and togavirus. Additional pathogenic microorganisms include bacteria, chlamydia, mycoplasma, protozoa, rickettsia and other unicellular microorganisms. Furocoumarins are also effective in inactivating Hepatitis B, Non-A Non B Hepatitis, and AIDS viruses. This inactivation method may also be used against uncharacterized infectious agents which may contain nucleic acid.

In addition to the furocoumarins, additives may be included which scavenge for singlet oxygen or other highly reactive oxygen containing species. Such additives include ascorbate, glutathione, sodium thionite, etc. In some instances these additives may have adverse efects, so that in each instance, their use will be determined empirically. Where such additives are present, they will be present in amounts ranging from about 20 ug to 20 mg per ml.

While the process of the earlier applications, and in some instances patents, works satisfactorily it has been found that it can be improved. Particularly when blood platelets are deprived of oxygen, there is some risk of impairment of cellular respiration. Put another way, there is a risk of deprivation of the mitochondria of oxygen, causing decreased aerobic metabolism and a relative increase in glycalysis resulting in a build-up of lactic acid and a corresponding decrease of pH. As this pH drop occurs the platelets deteriorate.

It has been found that two additional steps in the decontamination may be employed, either in combination or individually in order to minimize the risk of platelet deterioration. In particular, if one immediately follows the UVA irradiation with the addition of glucose, the damage to the blood components, and particularly to platelets is minimized. The range of glucose addition should be from about 100 ug/ml to about 100 mg/ml, preferably from about 300 ug./ml to about 1 mg/ml. When this occurs the evidence, as measured by pH data, shows a lack of any significant lactic acid buildup. The time of glucose addition can be immediately following the treatment up to about 5 hours after the treatment, preferably within the first hour after treatment.

As an additional improvement step, platelet damage is further minimized if there is a post-decontamination gassing, preferably with room air. The gassing may also occur with a combination of oxygen mixed with nitrogen, argon or other inert gases. One satisfactory method involves flushing with 2 psi air for up to an hour immediately following treatment.

The furocoumarins may be used individually or in combination. Each of the furocoumarins may be present in amounts ranging from about 0.01 ug/ml to 1 mg/ml, preferably from about 0.5 ug/ml to 100 ug/ml, there not being less than about 1 ug/ml nor more than about 1 mg/ml of furocoumarins. Various psoralen derivatives may be used, including but not limited to TMP, AMT, HMT, and 8-MOP. 8-MOP and TMP currently are FDA approved drugs for PUVA therapy in, for example, psoriasis. For this reason these compounds are preferred.

In carrying out the invention, the furocoumarins may be added to the biological composition by any convenient means in a manner substantially assuring the uniform distribution of the furocoumarins in the composition. The composition may then be irradiated using UVA (320 nm to 400 nm) under conditions ensuring that the entire composition is exposed to sufficient irradiation, so that the furocoumarins may react with any polynucleotide present to inactivate the polynucleotide. Depending upon the nature of the medium, particularly its opacity, as in the case of blood, the depth of the solution subject to irradiation will vary widely. Usually, the depth will be not less than about 0.025 millimeter, but may be as much as a centimeter or more. With whole blood, the depth will generally range from about 0.025 millimeter to 2.5 millimeters. The light which is employed will generally have a wavelength in the range of about 300 nm to about 400 nm. The intensity will generally range from about 0.1 mW/cm$^2$ to about 5 W/cm$^2$. In order to prevent denaturation, the temperature should be maintained below about 60° C., preferably below about 40° C., usually from about −10° C. to 30° C. The medium being irradiated may be irradiated while still, stirred or circulated, and may either be continuously irradiated or be subject to alternating periods of irradiation and non-irradiation. The circulation may be in a closed loop system or it may be in a single pass system ensuring that all of the sample has been exposed to irradiation. The total time for irradiation will vary depending upon the nature of the sample, the furocoumarin derivative used, the intensity and spectral output of the light source and the nature of the polynucleotides which may be present. Usually, the time will be at least 1 min. and not more than about 24 hrs., more usually from about 15 mins. to about 6 hrs. When circulating the solution, the rate of flow will generally be in the range of about 0.1 ml/min to 50 liters/min. It may be desirable to remove the unexpended psoralen and/or its photobreakdown products from the irradiation mixture. This can be readily accomplished by centrifugation, dialysis across an appropriately sized membrane, or ultrafiltration through an appropriately sized hollow fiber system. It may be desirable in certain applications to remove bound or unbound furocoumarins using antibodies, including monoclonal antibodies, either in solution or attached to a substrate.

The following examples are offered by way of illustration and not by way of limitation.

EXPERIMENTAL

The following experiments were performed in order to demonstrate the ability of the psoralen photoreaction to destroy microbial contaminants contained in whole blood and blood products.

(1) Feline rhinotracheitis virus, a member of the herpesvirus family, was added to heparinized whole rabbit blood in an amount that would give a final concentration of approximately $2 \times 10^7$ PFU/ml. 4'-hydroxymethyl-4,5',8-trimethylpsoralen (HMT) was added to a portion of the rabbit blood and aliquots were irradiated for various periods of time. To test for remaining live virus, duplicate plaque assays were performed using cultured feline cells (Fc3Tg) (ATCC CCL 176), with a methylcellulose overlay. Virus titers were obtained as the arithmetical mean of viral plaques observed in duplicate assay cultures 72 hours after exposure to test samples. The results are as follows:

The blood aliquot that received HMT only and no irradiation gave a titer of $5.3 \times 10^6$ PFU/ml. The aliquot that received HMT and five minutes of irradiation exhibited a titer of $4.5 \times 10^6$ PFU/ml. In the aliquot that received psoralen plus one hour of irradiation there was no detectable live virus remaining. The sensitivity of this assay should have permitted detection of residual virus at titers $1.0 \times 10^1$ PFU/ml. A blood sample which had received HMT and one hour of irradiation also showed no apparent damage to the red blood cells as judged by phase contrast microscope analysis and by absence of visible hemolysis. These data therefore demonstrate that high virus titers present in whole blood can be inactivated by psoralen plus light treatment which leaves the red cell component of the blood intact.

(2) In the second experiment Blue Tongue Virus (Serotype 11), a member of the reovirus family, and Feline Rhinotracheitis Virus, and Simian Virus 40 were added to a solution of Profilate (a commercial preparation of human clotting factor VIII produced by Alpha Therapeutics). The lyophilized preparation of Profilate (180 units) was dissolved in 10 ml of sterile water included with the commercial preparation. This solution was further diluted with barbital buffer (11.75 g sodium barbital and 14.67 g NaCl dissolved in 2 liters of deionized water and filtered through a 0.22 micron filter) to a final concentration of 5 units per milliliter. One portion (2 ml) was set aside at room temperature in the dark. This was sample #1. A second 2 ml portion was pumped through the apparatus described below for 1 hour with irradiation. This was sample #2. Through addition of appropriate amounts of reagents a third 2 ml portion was adjusted to contain 10 ug/ml AMT and 10 ug/ml HMT and was also irradiated for 1 hour. This was sample #3. All the samples were kept at 20° C. throughout the manipulations. The total elapsed time from dissolving of the lyophilized preparation to the completion of the clotting factor VIII assays was 6 and one-half hours.

The clotting factor VIII assays were performed at a variety of dilutions (ranging from 1:5 to 1:100) for each sample and were compared with the activity in normal human serum and with pooled normal human serum. The results are summarized in Table 1.

TABLE 1

Effect of Photochemical Inactivation Procedure and Its Components* on in vitro Activity of Factor VIII+

| | | | Sample | | |
|---|---|---|---|---|---|
| dilution | normal | pool | #1 F−, UVA− | #2 F−, UVA+ | #3 F+, UVA+ |
| 1:5 | 97 | 108 | 225 | 150 | 186 |
| 1:10 | 102 | 102 | 245 | 155 | 186 |
| 1:20 | 93 | 92 | 280 | 176 | 196 |
| 1:50 | 101 | 95 | 265 | 190 | 232 |
| 1:100 | — | 100 | 255 | 196 | 263 |
| Average | 98 | 99 | 254 | 173 | 213 |

*F = Furocoumarin;
UVA = long wavelength ultraviolet light;
+ Factor VIII activity expressed in % of normal activity.
100% = 1 U/ml of Factor VIII activity The sample that was subjected to the psoralen inactivation protocol (sample #3) retained 84% of the factor VIII activity that was present in the control sample (#1). This was higher than the product activity retained by the sample that was only irradiated (68% retained for sample #2) and indicates that the psoralen photochemistry has little or no effect on the activity of factor VIII.

Samples otherwise identical to samples 1, 2, and 3 above were seeded with $2 \times 10^6$ PFU/ml of Feline Rhinotracheitis Virus (FeRT), $1 \times 10^7$ PFU/ml of Blue Tongue Virus (BTV), and $4 \times 10^8$ PFU/ml of Simian Virus 40 (SV-40). Table 2 shows the results of the plaque assays on those samples.

TABLE 2

Effect of Photochemical Inactivation Procedure and its Components* on Infectivity of Virus in Factor VIII preparation.+

| | Sample 1 F−, UVA− | Sample 2 F−, UVA+ | Sample 3 F+, UVA+ |
|---|---|---|---|
| FeRT Titer | $8.6 \times 10^5$ | $3.5 \times 10^5$ | 0.0 |
| BTV Titer | $3.8 \times 10^7$ | $1.4 \times 10^7$ | $1.1 \times 10^2$ |
| SV-40 Titer | $2.5 \times 10^8$ | $1.6 \times 10^8$ | $1.2 \times 10^3$ |

*F = Furocoumarin;
UVA = long wavelength ultraviolet light.
+ Infectivity determined by plaque assays in tissue culture.

In the case of FeRT the number of detectable virus particles was reduced by more than five orders of magnitude to beneath the limit of detection in the plaque assay. The BTV infectivity was reduced by about five orders of magnitude to 110 PFU/ml. The SV40 infectivity was reduced to a titer of $1.2 \times 10^3$. Thus, it is shown that multiple, widely distinct types of virus can be simultaneously inactivated by at least five orders of magnitude in the presence of factor VIII, using the simple, convenient, brief process described above, with retention of at least 84% of factor VIII activity. Based on the above observations, it is predictable that by extending, repeating or modifying the treatment, the probability of an infectious virus particle remaining can be reduced to an arbitrarily low value. In this manner suitable safety margins can be achieved for any of the cited applications.

APPARATUS AND SYSTEM

Since whole blood exhibits very high optical density for longwave UV light (absorption is high for visible light in the 400 nm to 500 nm range), the blood was irradiated through a suitably short optical path length In this experiment blood was pumped through polyethylene capillary tubing of 0.875 millimeter inside diameter. The tubing was coiled around a 1.27 centimeter diameter tube and immersed in water which was maintained at 18° C. The blood was continuously circulated through the tubing by means of a peristaltic pump. The blood required aproximately 2.5 minutes for a complete cycle through the capillary tubing and was in the light beam for approximately 20% of the stated irradiation time. The light source was a low pressure mercury lamp filtered through a cobalt glass filter. The filter transmits light of approximately 320 nm–380 nm, with peak transmittance at 360 nm. The incident intensity at the sample was approximately 40 mW/cm$^2$.

It is evident from the above results, and in accordance with the subject invention, that polynucleotides in biochemical compositions can be inactivated to provide a safe composition for administration to a mammalian host. The proteins present in the composition retain their physiological activity, so that they can fulfill their physiological function in a mammalian host. The method is simple, rapid, and can be expanded to treat large samples The small amount of chemical reagent required will not generally be harmful to the host.

EXAMPLES OF IMPROVED METHOD OF PLATELET DECONTAMINATION

A series of experiments was performed to determine inactivation conditions which would minimize damage to platelets. In these experiments, platelet concentrates were treated under various conditions and stored at room temperature for 96 hrs following treatment. The platelet integrity was assessed by pH measurement and morphology evaluation at 24 hr intervals.

As shown in Table 3, UVA irradiation for 10 hrs can be deleterious to platelets. The pH of the treated platelets fell from 7.31 to 6.83 immediately following treatment while the pH of the control remained essentially unchanged. Prolonged storage (72 hrs) of treated platelets resulted in a drop of pH to 5.69. A platelet pH within the range of 6.7 to 7.4 is consistent with healthy platelets without a significant lactic acid build up.

In an attempt to reduce platelet injury during UVA irradiation, any possible short wavelength UV was blocked by irradiating through θ inch-thick acrylic sheets. Apparently, the platelet damage was not due to short wavelength UV. With irradiation in the presence of acrylic filters, the pH of the treated platelets dropped just as much (7.31 to 5.67) as without filters within 72 hrs following treatment.

Furthermore, flushing with $N_2$ did not protect platelets from injury due to 10-hr UVA irradiation, as judged by the pH decrease (7.28 to 5.73). Accordingly, as shown in Table 4, the morphology score of 10 hr-UVA treated platelets dropped drastically from 360 to 98–103 72 hrs following treatment, while the control platelets had scores above 200 after 96 hrs of storage.

The platelet damage due to UVA irradiation alone is proportional to the UVA irradiation time. By shortening the irradiation time to 6 hrs, the pH of the treated platelets remained essentially unchanged (7.2 to 7.50) immediately following treatment. Long term storage resulted in a decrease from 7.52 to 6.26. Irradiation under $N_2$ appeared to be advantageous for the shorter time of UVA irradiation. As shown in Table 3, the final pH after 96 hrs of storage is 6.96 if platelet concentrates were irradiated for 6 hrs under $N_2$. Accordingly, the morphology scores (Table 4) for the 6 hr-UVA treated platelets were above 200 even after 96 hrs of storage. These scores are comparable to those of the untreated control platelets.

Addition of 8-MOP to the irradiation system had essentially no effect on the pH of the platelet concentrates. As shown in Table 3, 6 hrs of irradiation under $N_2$ with 300 ug/ml of 8-MOP resulted in the pH drop from 7.55 to 6.89 after 96 hrs of storage. This is comparable to the pH change obtained in the absence of 8-MOP (7.54 to 6.96). Furthermore, UVA irradiation in the presence of 8-MOP has minimal additional effect on the morphology scores of treated platelets (Table 4). Thus it was concluded that UVA irradiation does have an effect on platelet concentrates. The effect could be minimized by irradiating in the substantial absence of oxygen.

In this improved process additional measures are taken to provide further protection for treated platelets from damage occurring during UVA irradiation and subsequent storage. Glucose is added in these examples to a final concentration of 1 mg/ml to treated platelet concentrates at the end of the treatment. As shown in Table 3, this appeared to have an effect on maintaining the pH of platelet concentrates above 7.0 upon prolonged storage The final pH after 96 hrs of storage following treatment was 7.11. In yet another improvement, since flushing with $N_2$ for 6.5 hrs resulted in an increase of 0.22 to 0.51 units in pH of treated platelet concentrates, the pH of the treated platelet concentrates can be brought back to its initial value by exchanging the $N_2$ with air. This was accomplished by flushing with 2 psi of air for an hour immediately following treatment. As shown in Table 3, the final pH of treated platelets after 96 hrs of storage was 7.15. Since both the glucose addition and air exchange had a positive effect on maintaining the pH of treated platelets upon storage without lowering their morphology scores (Table 4), these measures can be adopted as routine procedures for an improved photochemical decontamination protocol.

Finally, in order to eliminate the pH increase due to $N_2$ flushing during UVA irradiation, flushing with 2 psi of 5% $CO_2$ mixed with $N_2$ was tried. As shown in Table 3, the pH of treated platelet concentrates was 7.38 immediately following treatment and was 7.40 24 hrs thereafter. Furthermore, the pH was maintained at 7.30 even after 96 hrs of storage. The morphology scores (Table 4) of treated platelets were comparable to those of untreated control platelets. Therefore, subsequent experiments were carried out by flushing with 2 psi of 5% $CO_2$ and 95% $N_2$.

UVA-irradiation under 5% $CO_2$ and 95% $N_2$ appeared to allow longer irradiation time with maintenance of an acceptable solution pH. Data presented in Tables 3 and 4 shows that after 8 to 10 hrs of irradiation under 5% $CO_2$, the pH of treated platelet concentrates was maintained above 7.0 even after 48 hrs of storage, and the morphology scores were comparable to those of the control sample even at T72.

TABLE 3

Summary of Extracellular pH of Platelet Concentrates Treated Under Various Conditions

| | 8-MOP | glucose | air | TO | TE | T24 | T48 | T72 | T96 |
|---|---|---|---|---|---|---|---|---|---|
| Control | − | − | − | 7.54 | 7.56 | 7.59 | 7.61 | 7.65 | 7.69 |
| 10 hr-UVA | − | − | − | 7.31 | 6.83 | 6.21 | 5.72 | 5.69 | N.D. |
| 10 hr-UVA + acrylic | − | − | − | 7.31 | 6.80 | 6.24 | 5.75 | 5.67 | N.D. |
| 10 hr-UVA + $N_2$ | − | − | − | 7.28 | 7.50 | 6.55 | 5.85 | 5.73 | N.D. |
| 6 hr-UVA | − | − | − | 7.52 | 7.50 | 7.28 | 6.89 | 6.59 | 6.26 |
| 6 hr-UVA + $N_2$ | − | − | − | 7.54 | 7.93 | 7.41 | 7.26 | 7.12 | 6.96 |
| 6 hr-UVA + $N_2$ | + | − | − | 7.55 | 7.94 | 7.38 | 7.27 | 7.10 | 6.89 |
| 6 hr-UVA + $N_2$ | + | + | − | 7.52 | 8.03 | 7.43 | 7.26 | 7.20 | 7.11 |
| 6 hr-UVA + $N_2$ | + | + | + | 7.52 | 8.01 | 7.46 | 7.32 | 7.23 | 7.15 |
| 6 hr-UVA + $CO_2$ + $N_2$ | + | + | + | 7.52 | 7.38 | 7.40 | 7.43 | 7.44 | 7.30 |
| 8 hr-UVA + $CO_2$ + $N_2$ | + | + | + | 7.48 | 7.26 | 7.35 | 7.16 | N.D. | 6.65 |

TABLE 3-continued

Summary of Extracellular pH of Platelet
Concentrates Treated Under Various Conditions

| | 8-MOP | glucose | air | pH TO | TE | T24 | T48 | T72 | T96 |
|---|---|---|---|---|---|---|---|---|---|
| 10 hr-UVA + $CO_2$ + $N_2$ | + | + | + | 7.56 | 7.27 | 7.34 | 7.15 | 6.95 | 6.61 |

8-MOP was used at a final concentration of 300 μg/ml. Glucose was added at the completion of the treatment to a final concentration of 1 mg/ml. All gas flushing was done at 2 psi. TO = beginning of the treatment time. Time of treatment for different experiments is specified in the first column. TE = immediately after the end of treatment. T24, T48, T72 and T96 = 24 hrs, 48 hrs, 72 hrs, and 96 hrs after the beginning of the treatment. UVA = irradiation under UVA la mps (peak spectral output from 340 to 380 nm) at an intensity of 3.5–4.8 $mW/cm^2$. $N_2$ = 100% $N_2$ compressed gas (Liquid Carbonics. San Carlos. CA). $CO_2$ + $N_2$ = 5% $CO_2$: 95% $N_2$ custom-mixed compressed gas (Liquid Carbonics. San Carlos. CA). acrylic = ¼ inch thick sheet of polyacrylate plastic (TAP Plastics, San Leandro, CA). air = flushing at 2 psi with compressed air. N.D. = not determined.

TABLE 4

Summary of Morphology Scores of Platelet
Concentrates Treated Under Various Conditions

| | 8-MOP | glucose | air | Morphology Scores TO | TE | T24 | T48 | T72 | T96 |
|---|---|---|---|---|---|---|---|---|---|
| Control | — | — | — | 308 | 265 | 247 | 217 | 210 | 218 |
| 10 hr-UVA | — | — | — | N.D. | N.D. | 189 | 130 | 103 | N.D. |
| 10 hr-UVA + acrylic | — | — | — | N.D. | N.D. | 217 | 145 | 98 | N.D. |
| 10 hr-UVA + $N_2$ | — | — | — | 360 | N.D. | 217 | 94 | 103 | N.D. |
| 6 hr-UVA | — | — | — | 347 | 294 | 269 | N.D. | 271 | 211 |
| 6 hr-UVA + $N_2$ | — | — | — | 320 | 266 | 255 | 237 | 230 | 214 |
| 6 hr-UVA + $N_2$ | + | — | — | 309 | 245 | 267 | 236 | 234 | 234 |
| 6 hr-UVA + $N_2$ | + | + | — | 347 | 275 | 276 | N.D. | 290 | 234 |
| 6 hr-UVA + $N_2$ | + | + | + | 347 | 276 | 280 | N.D. | 250 | 232 |
| 6 hr-UVA + $CO_2$ + $N_2$ | + | + | + | 264 | N.D. | 226 | 273 | 218 | 212 |
| 8 hr-UVA + $CO_2$ + $N_2$ | + | + | + | 264 | N.D. | 200 | 228 | N.D. | 190 |
| 10 hr-UVA + $CO_2$ + $N_2$ | + | + | + | 276 | N.D. | 242 | 220 | 219 | 202 |

8-MOP was used at a final concentration of 300 μg/ml. Glucose was added at the completion of the treatment to a final concentration of 1 mg/ml. All gas flushing was done at 2 psi. TO = beginning of the treatment time. Time of treatment for different experiments is specified in the first column. TE = immediately after the end of treatment. T24, T48, T72 and T96 = 24 hrs, 48 hrs, 72 hrs, and 96 hrs after the beginning of the treatment. UVA = irradiation under UVA la mps (peak spectral output from 340 to 380 nm) at an intensity of 3.5–4.8 $mW/cm^2$. $N_2$ = 100% $N_2$ compressed gas (Liquid Carbonics. San Carlos. CA). $CO_2$ + $N_2$ = 5% $CO_2$: 95% $N_2$ custom-mixed compressed gas (Liquid Carbonics. San Carlos, CA). acrylic = ¼ inch thick sheet of polyacrylate plastic (TAP Plastics. San Leandro. CA). air = flushing at 2 psi with compressed air. N.D. = not determined.

Although the foregoing invention has been described in some detail by way of illustration and example for purposes of clarity of understanding, it will be obvious that certain changes and modifications may be practiced within the scope of the appended claims.

What is claimed is:

1. A method for decontaminating blood components suspected of containing viruses, said blood components being selected from the group consisting of red blood cells, platelets, blood clotting factors, plasma and immunoglobulins, without substantial impairment of the physiological activities of the treated blood components, said method comprising:
   (a) adding to a blood component selected from the group consisting of red blood cells, platelets, blood clotting factors, plasma and immunoglobulins at least one psoralen compound in an amount sufficient to inactivate substantially all contaminating viruses prevent; and thereafter
   (b) irradiating said psoralen treated blood component with long wavelength ultraviolet light under operating conditions which maintain the concentrations of reactive oxygen species at levels which do not substantially impair the physiological activity of the treated blood component, and wherein said irradiation is conducted for a time sufficient to inactivate substantially all contaminating viruses present; and thereafter
   (c) adding to said blood component glucose in a small but effective amount to minimize damage to said blood component.

2. The method of claim 1 wherein the amount of glucose added is from about 100 μg/ml to about 10 mg/ml.

3. The method of claim 2 wherein the amount of glucose added is from about 300 82 g/ml to about 1 mg/ml.

4. The method of claim 1 wherein said glucose addition occurs within from about 0 to about 5 hours after said irradiation.

5. The method of claim 1 wherein said glucose addition occurs within 1 hour after said irradiation.

* * * * *